(12) United States Patent
Rogatschnig

(10) Patent No.: US 8,057,488 B2
(45) Date of Patent: Nov. 15, 2011

(54) EPILATING APPARATUS AND COOLING/HEATING PAD FOR THE SAME APPARATUS

(75) Inventor: Johann Rogatschnig, Velden (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 190 days.

(21) Appl. No.: 12/305,443

(22) PCT Filed: Jun. 22, 2007

(86) PCT No.: PCT/IB2007/052420
§ 371 (c)(1),
(2), (4) Date: Dec. 18, 2008

(87) PCT Pub. No.: WO2008/010117
PCT Pub. Date: Jan. 24, 2008

(65) Prior Publication Data
US 2009/0209977 A1    Aug. 20, 2009

(30) Foreign Application Priority Data

Jun. 26, 2006 (EP) ..................... 06116049

(51) Int. Cl.
*A61B 17/50* (2006.01)
(52) U.S. Cl. ....................................................... 606/133
(58) Field of Classification Search ................... 606/131, 606/133
See application file for complete search history.

(56) References Cited

U.S. PATENT DOCUMENTS

| 5,827,307 A * | 10/1998 | Tipton .......................... 606/160 |
| 5,849,018 A | 12/1998 | Rosson et al. |
| 6,681,590 B1 | 1/2004 | Jones |
| 2002/0120278 A1 | 8/2002 | Cense et al. |

FOREIGN PATENT DOCUMENTS

| DE | 10020819 A1 | 11/2001 |
| EP | 0348862 A2 | 1/1990 |
| WO | 2000054685 A2 | 9/2000 |
| WO | 2000076363 A1 | 12/2000 |
| WO | 2005000185 A2 | 1/2005 |

* cited by examiner

*Primary Examiner* — Ryan Severson

(57) ABSTRACT

An epilating apparatus includes a compartment for receiving a cooling/heating pad. The cooling/heating pad includes a bag portion containing a cooling/heating medium and a fixing portion for removably fixing the cooling/heating pad to the epilating apparatus.

8 Claims, 4 Drawing Sheets

EPILATING APPARATUS AND COOLING/HEATING PAD FOR THE SAME APPARATUS

FIELD OF THE INVENTION

The invention relates to an epilating apparatus, a cooling/heating pad for an epilating apparatus, and a cooling/heating pad add-on kit for an epilating apparatus.

BACKGROUND OF THE INVENTION

An epilating apparatus comprising an auxiliary member for cooling the skin is for example known from WO-A-00/76363. With the known epilating apparatus hairs are mechanically extracted from the skin. The hair removing member of the known epilating apparatus comprises a series of clamping discs which are rotatably supported in an epilation head. During rotation of the clamping discs the clamping discs are tiltable in pairs, from a hair catching position, in which hair catching spaces are present between the pairs of clamping discs, to a clamping position in which the pairs of clamping discs are clamped against each other near their edges. Hairs that penetrate the hair catching spaces when the clamping discs are in the hair catching positions are subsequently clamped between the clamping discs and extracted from the skin under the influence of the rotating movement of the clamping discs.

The auxiliary member of the known epilating apparatus is provided with a skin contact element and a holder which is in thermal contact therewith. In the holder there is provided a substance having a comparatively high cold capacity. The auxiliary member is detachably coupled to a main housing of the hair removing device. Before using the hair removing device, the substance should be cooled to a comparatively low temperature by placing the auxiliary member, for example, in a refrigerator for some time. If the auxiliary member is coupled to the main housing, the skin contact element is situated, viewed in a direction wherein the hair removing device is to be displaced over the skin, directly in front of the hair removing member. Consequently, during displacing the hair removing device over the skin, the skin is first cooled by the auxiliary member and immediately after that treated by the hair removing member.

By previously cooling the skin the pain that is usually felt when hairs are extracted is masked. This masking effect can be attributed to the fact that pain stimuli generated during extracting the hairs by pain receptors present around the hairs, are only partially passed on via the nervous system because said nervous system is partially blocked to pain stimuli by the cold stimuli already present in the nerves system and generated by the cold receptors present around the hairs. By virtue of this masking effect the extraction of hairs is experienced as considerably less painful.

A similar pain reduction can be reached by heating the skin before it is treated. Additionally or alternatively it is also possible to cool or heat the skin after treatment. This also reduces the pain and can, for example, be realized by mounting the auxiliary member behind the epilating area with reference to the moving direction.

However, there is a problem in that the known auxiliary member and therefore the whole known epilating apparatus is costly. The known attempts to heat the skin before treatment are also costly.

It is therefore the object of the invention to provide a cheaper possibility for cooling/heating the skin to be treated.

SUMMARY OF THE INVENTION

The above object is solved by an epilating apparatus comprising a compartment for receiving a cooling/heating pad. The compartment accommodates the pad in such a way that, when the epilating apparatus is in an operating position relative to the skin, the pad is at least partially in direct or indirect thermal contact with the skin. As regards the compartment, such a compartment can be formed within a stiff overall housing, for example between a main body and a rigid sleeve attached thereto. However, it is also possible that the compartment is provided within a flexible bag-like housing which is intended to receive a state of the art epilating apparatus having no cooling/heating means and a separate cooling/heating pad. In such a case the flexible bag-like housing can, for example, be made of a textile or the like and can also function as a connector for the state of the art epilating device and the cooling/heating pad.

At least during use of the epilating apparatus it is preferred that a cooling/heating pad is removably arranged within the compartment. The term cooling/heating pad is intended to cover any member that does not comprise a completely rigid or substantially undeformable housing or covering portion, but comprises a cushion-like member having a deformable or flexible housing or covering portion accommodating a heating or cooling medium. The deformability or flexibility of the cooling/heating pad is an important advantage, because it allows a better contact of the cooling/heating pad with the skin during operation, so that cooling/heating of the skin is improved when the cooling/heating pad is directly in contact with the skin during operation. It is also possible that a core of the cooling/heating pad is surrounded at least partially by a flexible material to form the cooling heating pad. Furthermore, the cooling/heating pad can be insulated at least partially. For example, the cooling/heating pad can be made of a welded plastic foil which at least partially is filled by a cooling/heating medium having a comparatively high cold/heat capacity. Such a cooling/heating pad can be produced significantly cheaper than the known cooling members, and therefore the total costs are reduced. As with the known epilating apparatus mentioned at the beginning, the cooling/heating pad should be cooled to a comparatively low temperature by placing the cooling pad, for example, in a refrigerator for some time, before the epilating apparatus is used. Alternatively, the cooling/heating pad can be placed, for example, in a microwave, if it is desired to heat the skin before treatment to reduce the pain.

With preferred embodiments of the epilating apparatus in accordance with the invention, the cooling/heating pad comprises a bag portion containing a cooling/heating medium and a fixing portion for fixing the cooling/heating pad within the compartment. Also in this case the whole cooling/heating pad can, for example, be made by suitably welding a plastic foil. Of course it is also possible that the cooling/heating pad is formed without welding, for example by molding. It is preferred that the dimensions of the cooling/heating pad are at least essentially adapted to the dimension of the compartment. It is further preferred, but not mandatory, that the fixing portion contains no cooling/heating medium.

It is preferred for the epilating apparatus in accordance with the invention that the fixing portion of the cooling/heating pad at least partially is a flat portion. In such a case the fixing portion is preferably arranged within a handle portion of the epilating apparatus, wherein the flat fixing portion makes it possible to keep the dimensions of the handle portion so small that the handle portion can be gripped easily.

With highly preferred embodiments of the epilating apparatus in accordance with the invention, the cooling/heating pad contains a cooling/heating medium which comprises a gel. In such a case the cooling/heating pad can be referred to as a gel pad. Gel pads as such are known to be suitable for cooling or heating, for example, parts of the body, particularly in case of an injury. Any gel known to the person skilled in the art in this connection can be used as cooling/heating medium for the cooling/heating pad.

Furthermore, it is preferred that a ledge provided in the compartment interacts with the fixing portion of the cooling/heating pad. The ledge can, for example, be a bolt that extends through a hole provided in the fixing portion of the cooling/heating pad and additionally connects different parts of the epilating apparatus, for example a main body and a sleeve. In such a case the fixing portion of the cooling/heating pad can be clamped between the sleeve and the main body. It is also possible, that the fixing portion of the cooling/heating pad comprises no hole, but is fixed by clamping only.

In accordance with a further development of the epilating apparatus in accordance with the invention the compartment is formed between a main body of the epilating apparatus and a sleeve. The sleeve can, for example, be a plastic part which preferably also forms at least a section of the handle of the epilating apparatus. For example, the ledge mentioned above and provided in the compartment can be capable for securing the sleeve to the main body. However, this is not compulsory and the sleeve can be attached to the main body in any suitable manner. If the ledge is provided on the sleeve, it can, for example, engage into a recess provided in the main body. Such a connection can be made, for example, by force and/or form closure. Furthermore, it is preferred that the sleeve is movable with respect to the main body. The sleeve can be completely detachable or movable via, for example, a sliding or hinging movement. If the sleeve is movable with respect to the main body, it is easier to remove and insert the cooling/heating pad.

With preferred embodiments of the epilating apparatus in accordance with the invention the sleeve at least partially comprises an insulation. Such an insulation on one hand keeps the cooling/heating pad cool/hot for a longer period and on the other hand guarantees that the hands do not become too cold/hot during use of the epilating apparatus. Any suitable insulation material can be used for this purpose, for example, plastic foams, polystyrene and the like.

Particularly in connection with add-on kits it is also possible that the compartment is formed within pick-up means surrounding the epilating apparatus at least partially. In such a case the epilating apparatus in accordance with the invention is formed by a state of the art epilating apparatus comprising no compartment and the pick-up means.

Furthermore, it is preferred for the epilating apparatus in accordance with the invention, that the cooling/heating pad comprises an active cooling/heating portion arranged adjacent to an active epilating portion. The active cooling/heating portion is preferably arranged to directly contact the skin. It is also possible, that the active epilating portion is surrounded completely or at least in part by the active cooling/heating portion. In such a case it is also possible to use more than one cooling/heating pad, for example one on each side of the active epilating portion.

To solve the above object, the invention also provides a cooling/heating pad for an epilating apparatus, wherein the cooling/heating pad comprises a bag portion containing a cooling/heating medium and a fixing portion for fixing the cooling/heating pad to the epilating apparatus. Such a cooling/heating pad is suitable to be used with the epilating apparatus described above. As already mentioned, the cooling/heating pad can, for example, be made of a welded plastic foil. In any case the cooling/heating medium should have a comparatively high cold/heat capacity to store a sufficient amount of cold/heat. As regards the cooling/heating pad and the preferred embodiments thereof mentioned below, reference is again made to the above description, to avoid repetitions.

With preferred embodiments of the cooling/heating pad in accordance with the inventions, the cooling/heating medium comprises a gel. In such a case the cooling/heating pad can be referred to as a gel pad.

In accordance with a further development of the cooling/heating pad in accordance with the invention, the fixing portion comprises at least one recess intended to receive at least one ledge of the epilating apparatus.

Furthermore, it is preferred for the cooling/heating pad in accordance with the invention that the fixing portions at least partially is a flat portion.

The invention is also directed to a cooling/heating pad add-on kit for an epilating apparatus, the cooling/heating pad add-on kit comprising a cooling/heating pad and pick-up means for removably picking up the cooling/heating pad and the epilating apparatus. For example, it is possible that a compartment for receiving the cooling/heating pad is provided within a bag which is further intended to receive a state of the art epilating apparatus having no cooling/heating. The bag can be a flexible bag, for example, be made of a textile or the like. Alternatively, it is possible that the bag is made from a relative stiff material like plastic. The pick-up means can function as a connector for the state of the art epilating device and the cooling/heating pad.

These and other aspects of the invention will be apparent from and elucidated with reference to the embodiments described hereinafter.

DESCRIPTION OF PREFERRED EMBODIMENTS

Figure 1:
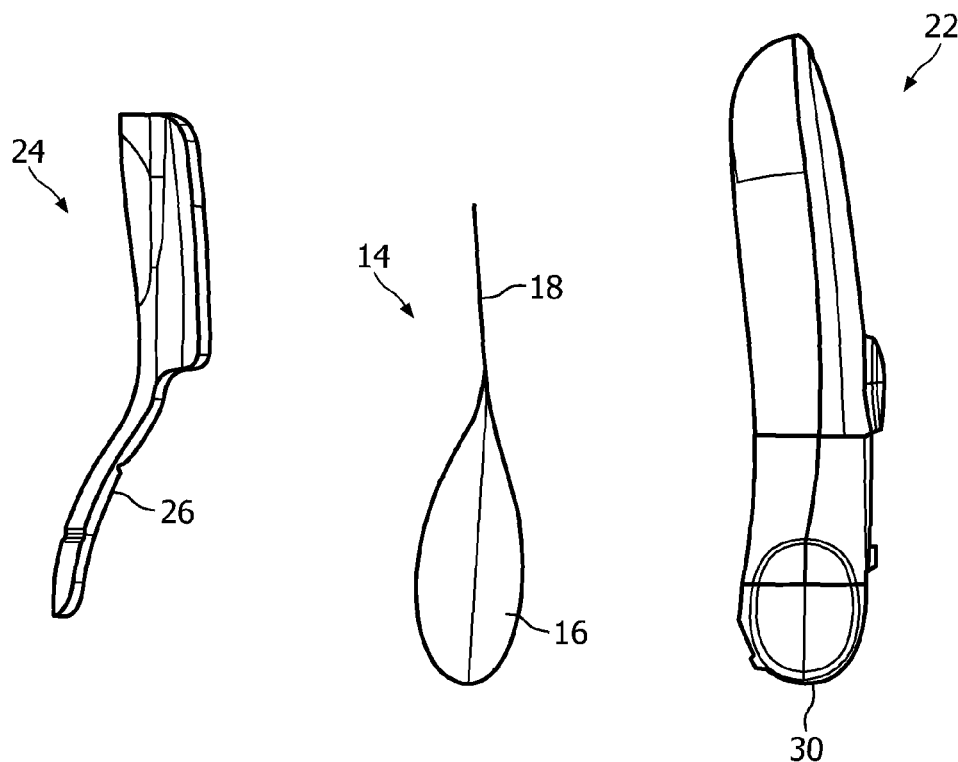
FIG. 1 shows side views of a main body, a cooling/heating pad, and a sleeve of an epilating apparatus in accordance with the invention.

In the Figures similar reference numerals refer to similar components which at least in some cases are described only once.

In the following, reference is made to FIGS. 1 through 5 simultaneously.

The illustrated apparatus consists of a main body 22 comprising an active epilating portion 30, a cooling/heating pad 14, and a sleeve 24.

Figure 2:
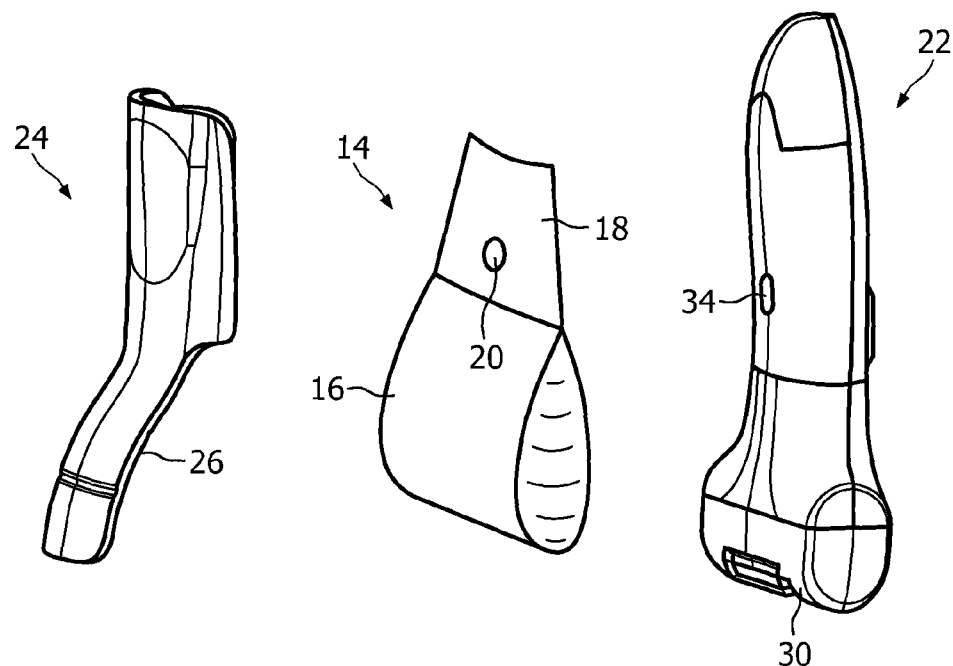
FIG. 2 shows perspective views of the main body, the cooling/heating pad, and the sleeve of FIG. 1.
Figure 3:
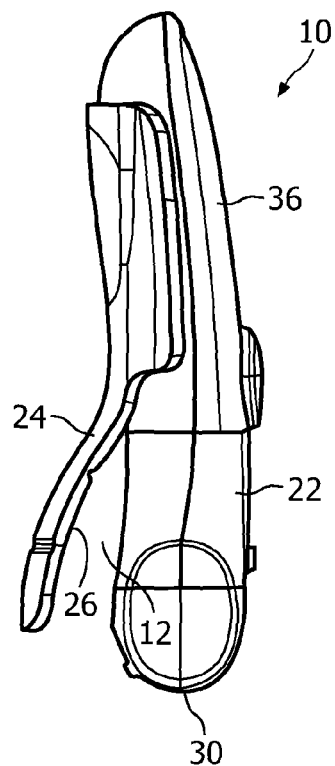
FIG. 3 shows a side view of an epilating apparatus consisting of the main body and the sleeve shown in FIGS. 1 and 2, wherein the cooling/heating pad is removed or not yet inserted.

As may be best seen in FIG. 2 the cooling/heating pad comprises a flat fixing portion 18 and a bag portion 16 containing a cooling/heating medium. The cooling/heating medium is preferably a gel comprising a sufficiently high cold/heat capacity for storing cold, if the cooling/heating pad 14 is for example placed in a refrigerator, or for storing heat, if the cooling heating pad 14 is for example placed in a microwave. The cooling/heating pad 14 is made by suitably welding a plastic foil, wherein the last weld seam is provided after the gel has been inserted in the bag portion 16. In the flat fixing portion 18 there is provided a recess 20 in form of a hole. The cooling/heating pad 14 is intended to be inserted into a compartment 12 (see FIG. 3) provided between the main body 22 and the sleeve 24 is attached to the main body 22.

The sleeve 24 can be attached to the main body 22 via a ledge 32 (see FIG. 5) provided on the sleeve 24 and intended to engage with form and/or force closure into a recess 34 (see FIG. 2) provided in the main body 22.

To insert the cooling/heating pad 14 into the compartment 12, the sleeve 24 which comprises an insulation 26 is detached from the main body 22 as a first step. Then, the hole 20 provided in the fixing portion 18 of the cooling/heating pad 14 is aligned with the recess 34 provided in the main body 22. In this condition the sleeve 24 is attached by inserting the ledge or bolt 32 through the hole 20 and into the recess 34.

Figure 4:
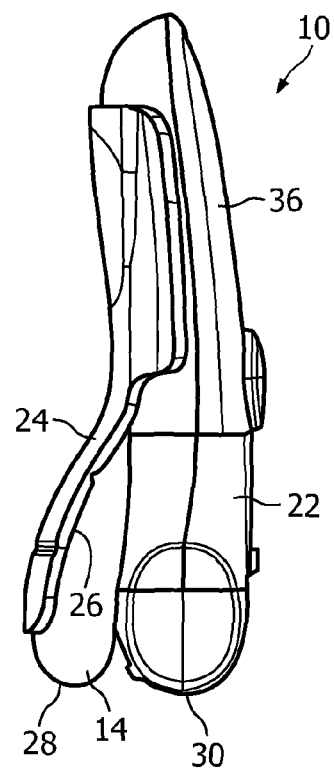
FIG. 4 shows a side view of an epilating apparatus consisting of the main body, the sleeve, and the cooling/heating pad shown in FIGS. 1 and 2, wherein the cooling/heating pad is inserted into a compartment.
Figure 5:
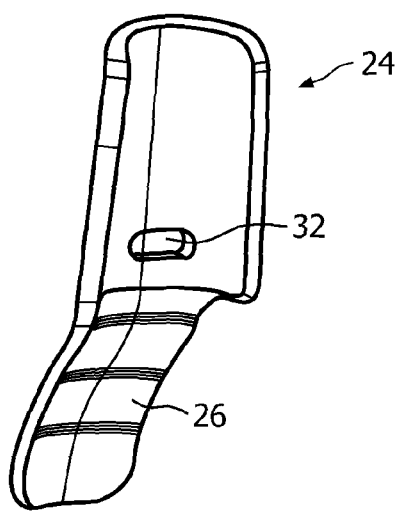
FIG. 5 shows a further perspective view of the sleeve used for the epilating apparatus shown in FIGS. 1 to 4.

The result of this operation is shown in FIG. 4. The flat fixing portion 18 of the cooling/heating pad which is clamped between the sleeve 24 and the main body 22 contributes to keep the dimensions of a handling portion 36 such that this handling portion 36 can be easily gripped. The bag portion 16 of the cooling/heating pad 14 forms an active cooling/heating portion 28 located adjacent to the active epilating portion 30. Due to the insulation 26 provided at least adjacent to the bag portion 16 of the cooling/heating pad 14, the hands of the user do not become too cold/hot during use of the epilating apparatus.

Figure 6:
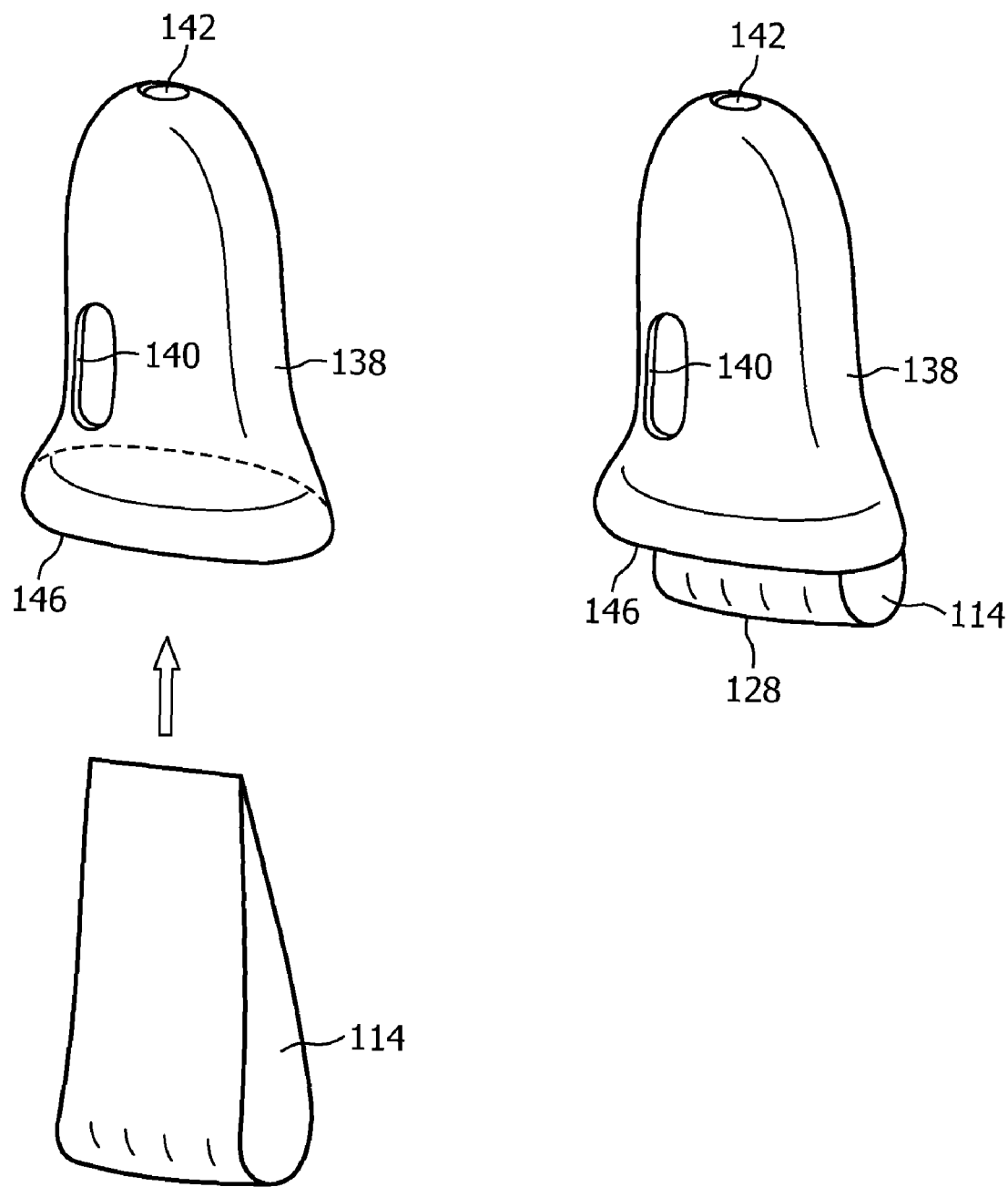
FIG. 6 shows a cooling/heating pad add-on kit in accordance with the invention.

FIG. 6 shows a cooling/heating pad add-on kit in accordance with the invention. The cooling/heating pad add-on kit consists of a cooling/heating pad 114 and pick-up means 138 for removably picking up the cooling/heating pad 114. With the illustrated embodiment, the pick-up means 138 are bag-like and are made of a flexible material, particularly formed from a textile. The pick-up means 138 comprise an aperture 140 intended to be aligned with one or more control elements 144 (shown in FIG. 7) only of a state of the art epilating apparatus. Furthermore, there is provided an aperture 142 through which, for example, a power plug can extend. The cooling/heating pad 114, which preferably is a gel pad, is inserted into the pick-up means 138 via a main aperture 146. The longitudinal dimensions of the bag-like pick-up means 138 and the cooling/heating pad 114 are preferably selected such that an active cooling/heating portion 128 intended to contact the skin protrudes. At least in some cases there may be provided additional connection means, for example hook and loop fastener, to connect the cooling/heating pad 114 and the pick-up means 138.

Figure 7:
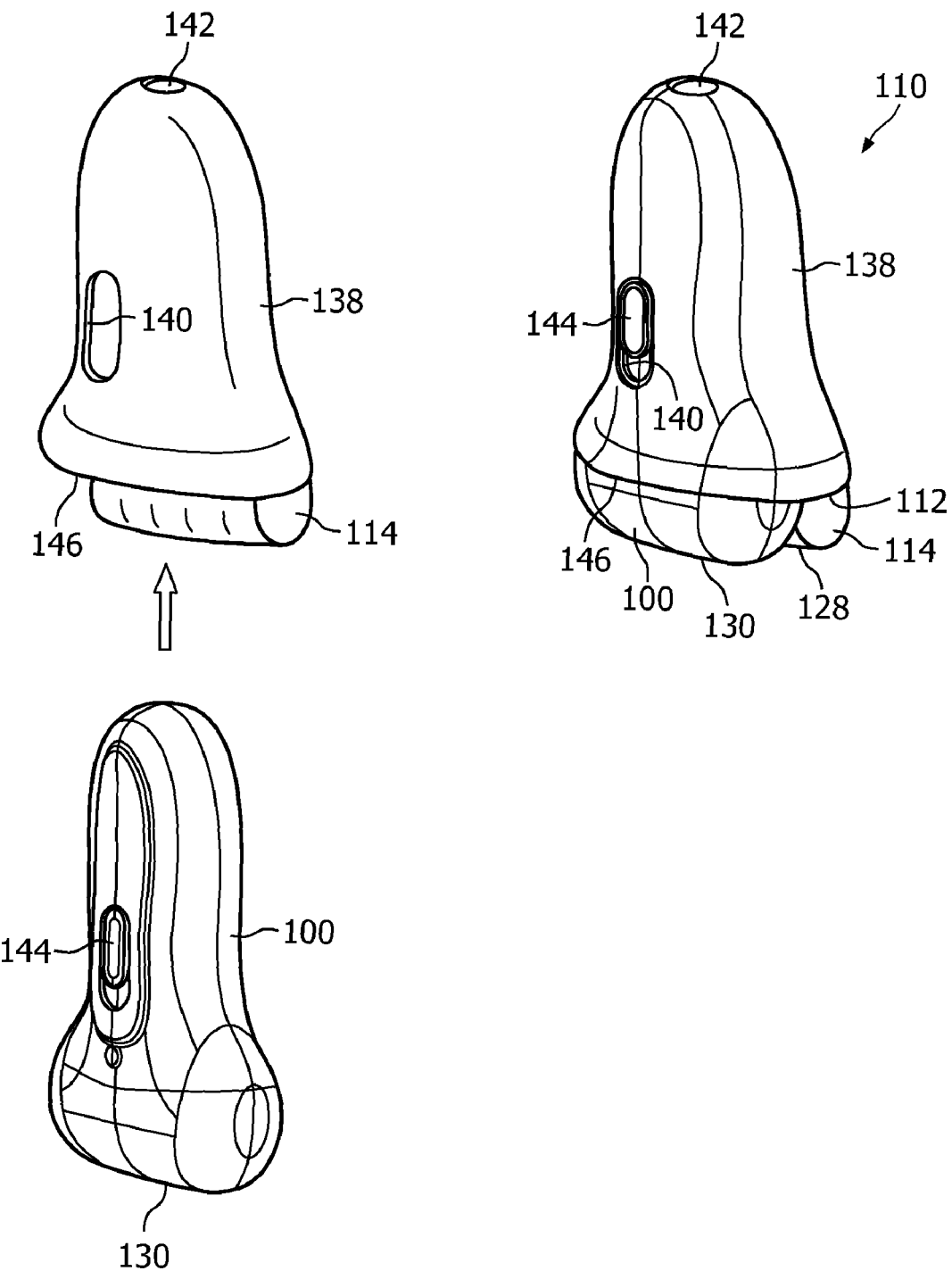
FIG. 7 shows the use of the cooling/heating pad add-on kit in accordance with FIG. 6 to realize an epilating apparatus in accordance with the invention.

FIG. 7 shows the use of the cooling/heating pad add-on kit 114, 138 in accordance with FIG. 6 to realize an epilating apparatus 110 in accordance with the invention. To achieve this, a state of the art epilating apparatus 100 comprising no cooling/heating means is inserted into the pick-up means 138. Particularly if the pick-up means 138 are flexible at least partially, the three components can be connected via force closure. Additionally or alternatively there can be provided further means, for example hook and loop fastener, to secure the state of the art epilating apparatus 100 within the bag-like pick-up means 138. The whole arrangement is such that an active epilating portion 130 is arranged adjacent to an active cooling/heating portion 128 of the cooling/heating pad 114. Therefore, the space between the state of the art epilating apparatus 100 and the pick-up means 138 which accommodates the cooling/heating pad 114 can be referred to as a compartment 112 of the epilating apparatus 110 in accordance with the invention.

Finally, it is to be noted that equivalents and modifications not described above may also be employed without departing from the scope of the invention, which is defined in the accompanying claims.

The invention claimed is:

1. An epilating apparatus comprising:
   a housing including a recess;
   a cooling/heating pad; and
   a sleeve which is removably connected to the housing to form a compartment for removably receiving the cooling/heating pad, the sleeve having a ledge extending from a surface of the sleeve
   wherein the cooling/heating pad is removably connected between the sleeve and the housing so that the sleeve, a fixing portion of the cooling/heating pad, and the housing are removably connected to each other,
   wherein the cooling/heating pad comprises a bag portion containing a cooling/heating medium and a fixing portion for fixing the cooling/heating pad within the compartment,
   wherein the fixing portion of the cooling/heating pad at least partially is a flat portion that includes a hole; and
   wherein the ledge of the sleeve is configured to pass through the hole of the flat portion and engage the recess of the housing for removably connecting together the sleeve, the flat portion and the housing.

2. The epilating apparatus according to claim 1, wherein the cooling/heating pad is removably arranged in the compartment.

3. The epilating apparatus according to claim 2, wherein the cooling/heating pad contains a cooling/heating medium which comprises a gel.

4. The epilating apparatus according to claim 1, wherein a ledge provided in the compartment interacts with the fixing portion of the cooling/heating pad.

5. The epilating apparatus according to claim 1, wherein the sleeve at least partially comprises an insulation.

6. The epilating apparatus according to claim 1, further comprising an epilating portion extending out of the housing for contacting a skin surface, wherein the sleeve completely surrounds the housing, and wherein a portion of the cooling/heating pad extends out of the housing adjacent to epilating portion for contacting the skin surface.

7. A cooling/heating pad for an epilating apparatus having a recess, the cooling/heating pad comprising:
   a bag portion containing a cooling/heating medium; and
   a fixing portion for fixing the cooling/heating pad to the epilating apparatus between a sleeve having a ledge and the epilating apparatus,
   wherein the sleeve, the fixing portion and the epilating apparatus are removably connected to each other, and
   wherein the fixing portion at least partially is a flat portion that includes a hole for passage of the ledge of the sleeve through the hole and engagement of the ledge with the recess of the epilating apparatus for removably connecting together the sleeve, the flat portion and the epilating apparatus.

8. The cooling/heating pad according to, claim 7, wherein the cooling/heating medium comprises a gel.

* * * * *